United States Patent [19]
Feder et al.

[11] Patent Number: 5,132,214
[45] Date of Patent: Jul. 21, 1992

[54] LARGE SCALE PRODUCTION OF PLASMINOGEN ACTIVATOR FROM NORMAL HUMAN COLON CELLS

[75] Inventors: Joseph Feder, St. Louis; Nicholaos K. Harakas, Chesterfield; Jon P. Schaumann, Kirkwood; Daniel T. Connolly, Manchester; Arthur J. Wittwer, Ellisville, all of Mo.

[73] Assignee: Monsanto Company, St. Louis, Mo.

[21] Appl. No.: 849,933

[22] Filed: Apr. 9, 1986

[51] Int. Cl.$^5$ .................... C12P 21/00; C07K 3/28
[52] U.S. Cl. .................... 435/70.3; 435/212; 435/219; 530/395; 424/94.63; 424/94.64; 514/8
[58] Field of Search .............. 435/68, 70.3, 212, 215, 435/216, 219, 240.2, 240.21, 240.23, 814, 815, 948; 530/395, 412, 413, 415, 417; 514/8, 21, 822; 424/94, 94.63, 94.64

[56] References Cited

U.S. PATENT DOCUMENTS

| | | | |
|---|---|---|---|
| 3,904,480 | 9/1975 | Hull et al. | 435/215 |
| 4,190,708 | 2/1980 | Kuo et al. | 435/215 |
| 4,335,215 | 6/1982 | Tolbert et al. | 435/241 |
| 4,505,893 | 3/1985 | Mori et al. | 424/94 |
| 4,537,860 | 8/1985 | Tolbert et al. | 435/240 |
| 4,550,080 | 10/1985 | Hasegawa et al. | 435/212 |
| 4,661,453 | 4/1987 | Pollard | 435/212 |
| 4,751,084 | 6/1988 | Feder et al. | 435/212 |

FOREIGN PATENT DOCUMENTS

| | | |
|---|---|---|
| 41766 | 12/1981 | European Pat. Off. |
| 117059 | 8/1984 | European Pat. Off. |
| 187779 | 10/1984 | Japan |
| 2119804 | 11/1983 | United Kingdom |

OTHER PUBLICATIONS

Corsanti et al., J. Natl. Cancer Inst. vol. 65(2), 345-351, 1980.
Rijkin and Collen et al., J. Biol. Chem. vol. 256(13), 7035-41, 1981.
Tissot et al., Prog. Fibrinolysis vol. 6, 133-135, 1983.
Goldfarb et al., Biochemistry, vol. 19(24), 5463-5471, 1980.
Tissot et al., "Characterization of Plasminogen Activators from Normal Human Breast and Colon and From Breast and Colon Carcinomas", Int. J. Cancer vol. 34, 295-302, 1984.
Rijken et al., "Purification and Partial Characterization of Plasminogen Activator from Human Uterine Tissue", Biochim Biophy Acta, vol. 580, 140-153, 1979.
Brouty-Boye et al, "Biosynthesis of Human Tissue-Type Plasminogen Activator by Normal Cells", Biotechnology, vol. 2, 1058-1062, 1984.
Pohl et al., "Tissue plasminogen activator: peptide analysis confirm an indirectly derived amino acid sequence, identify the active site serine residue, establish glycosylation sites and localize variant differences", Biochemistry, vol. 23(16) 3701-3707, 1984.
Shing et al., "Human and Bovine Milk Contain Different Sets of Growth Factors", Endocrinology, vol. 115(1), 273-282, 1984.
Kluft et al., Adv. Biotech. Proc. 2, Alan R. Liss, Inc., 1983, pp. 97-110.
Pennica et al., Nature 301, 214-21 (1983).
Vehar et al., Biotech. 2(12), 1051-57 (1984).
Collen et al., Circulation 70(16), 1012-17 (1984).
Pohl et al., FEBS Lett. 168(1), 29-32 (1984).
Husain et al., Proc. Natl. Acad. Sci. USA 78(7), 4265-69 (1981).
Schleef et al., Thromb. Haemos. 53(1), 170-175 (1985).

*Primary Examiner*—John Doll
*Assistant Examiner*—Gail Poulos
*Attorney, Agent, or Firm*—Scott J. Meyer

[57] ABSTRACT

Plasminogen activators (PA) are obtained from cultured normal human colon cells which are adaptable to large scale production. A purified tissue PA (t-PA) is obtained from CCD-18Co normal human colon fibroblast cells which shows chemical differences from Bowes melanoma t-PA.

6 Claims, 5 Drawing Sheets

FIG. 4.a
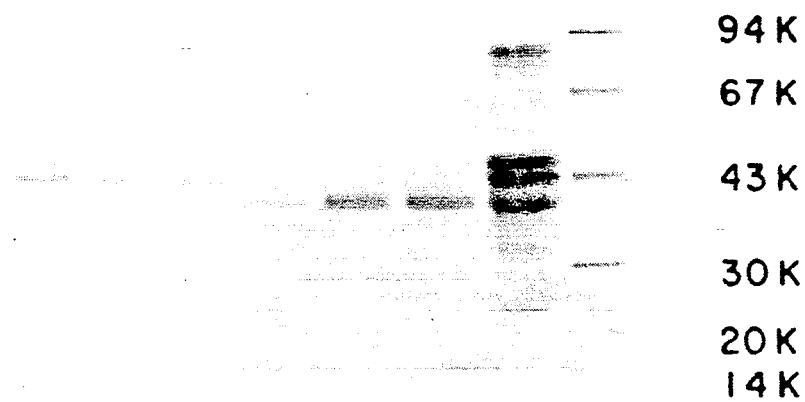
FIG. 4.b
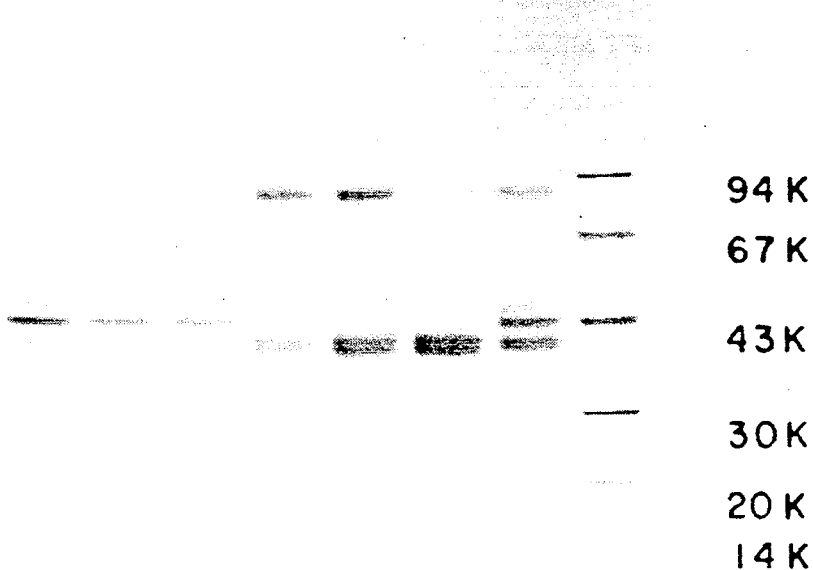

LARGE SCALE PRODUCTION OF PLASMINOGEN ACTIVATOR FROM NORMAL HUMAN COLON CELLS

BACKGROUND OF THE INVENTION

This invention relates to plasminogen activators which are useful thrombolytic agents. More particularly, this invention relates to the large scale production of plasminogen activators from cultured normal human colon cells.

It is known that plasminogen activators (PA) are widely distributed throughout the body and can be purified from tissue extracts. Typical examples of tissue sources are kidney and lung tissues. The best characterized of these plasminogen activators fall into two major groups, urokinase-type plasminogen activator (u-PA) and tissue-type plasminogen activator (t-PA). u-PA and t-PA are present in ng/ml concentrations in human plasma but are immunologically unrelated. t-PA has been demonstrated to have higher affinity for fibrin than u-PA. u-PA products isolated and purified from human urine and from mammalian kidney cells are pharmaceutically available as thrombolytic agents.

Due to the extremely low concentration of t-PA in blood and tissue extracts, other sources and means of producing this preferred thrombolytic agent have been sought after.

One method of producing t-PA on a large scale comprises isolating the protein from the culture fluid of human melanoma cells grown under in vitro cell culture conditions. An established human melanoma cell line (Bowes) has been used for this purpose. See, for example, European Patent Application 41,766, published Dec. 16, 1981; Rijken and Collen, *J. Biol. Chem.* 256(13), 7035-7041 (1981); and Kluft et al., *Adv. Biotech. Proc.* 2, Alan R. Liss, Inc., 1983, pp. 97-110. Genetic information from this cell line also has been embodied in *E. coli* by conventional recombinant DNA gene splicing methods to permit the production of the t-PA protein by that microorganism. See, for example, UK Patent Application 2,119,804, published Nov. 23, 1983; Pennica et al., *Nature* 301, 214-221 (1983); and Vehar et al., *Biotech.* 2(12), 1051-1057 (1984). Such t-PA material from Bowes melanoma has been administered to humans with some measure of effectiveness. See Collen et al., *Circulation* 70 16, 1012-1017 (1984).

Notwithstanding the apparent utility of the t-PA derived from Bowes melanoma, the use of cancer cells or genetic information derived from cancer cells can raise uncertain drug regulatory problems in the therapeutic use of such materials. Thus, it is known that cancer cells (transformed cells) can produce human transforming growth factors. See, for example, Delarco and Todaro, *Proc. Natl. Acad. Sci. USA* 75, 4001-4005 (1978), and Todaro et al., *Ibid.*, 77, 5258-5262 (1980). Even the smallest amount of residual DNA from the cancer cells can be integrated into and expressed in the *E. coli* or genetically engineered mammalian cells, thereby raising the possibility of harmful effects if t-PA from such source is administered to the patient. Although the risks may be small by judicious use of various purification techniques and appropriate monitoring of patients, it still would be preferable to use a t-PA that was not derived from cancer cells either directly or indirectly. The possible presence of viral genetic material or oncogene product can raise significant objections to the use of clinical material thus derived from transformed cells.

Accordingly, the production of tissue-type plasminogen activators from normal human cells on a large scale would be highly desirable. Cultured normal human cells have been used as a source of t-PA as can be seen from U.S. Pat. Nos. 4,505,893 and 4,550,080. Although various cell sources are mentioned in said patent, apparently only primary embryonic (or fetal) kidney, lung, foreskin, skin and small intestines (Flow Laboratories) were actually cultured according to the disclosure. Brouty-Boye et al., *Biotech.* 2(12), 1058-1062 (1984), also disclose the use of normal human embryonic lung cells for the production of t-PA. Rijken and Collen, *J. Biol. Chem.* 256 (13), 7035-7041 (1981), and Pohl et al., *FEBS Lett.* 168(1), 29-32 (1984), disclose the use of human uterine tissue as a t-PA source material.

BRIEF DESCRIPTION OF THE INVENTION

In accordance with the present invention, plasminogen activators (PA) are obtained from cultured normal human colon cells which are adaptable to large scale production. A purified colon t-PA is obtained which shows chemical differences from the Bowes melanoma t-PA in oligosaccharide structure as disclosed in copending application Ser. No. 834,080, filed Feb. 26, 1986, now U.S. Pat. No. 4,751, 084 assigned to the common assignee and incorporated herein by reference. The present process for producing the human plasminogen activator comprises culturing in vitro normal human colon cells in nutrient culture medium, subjecting the resulting conditioned medium to a first affinity chromatography with zinc chelate-agarose and then a second affinity chromatography with material selected from the group consisting of (a) concanavalin A-agarose, (b) fibrin-Celite, and (c) fibrin-agarose, followed by TSK 3000 SW size exclusion high performance liquid chromatography and p-aminobenzamidineagarose affinity chromatography and recovering the resulting plasminogen activator fractions.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings of: t-PA colorimetric assay results, High Performance Liquid Chromatography (HPLC) and Con A-Sepharose® chromatography elution profiles, and photographs of SDS-PAGE gels in which:

FIG. 4 shows the reduced SDS-PAGE of HPLC fractions obtained during the separations of FIG. 2

FIG. 4a shows the reduced SDS-PAGE of HPLC fractions obtained during the separations of FIG. 3.

Figure 1:
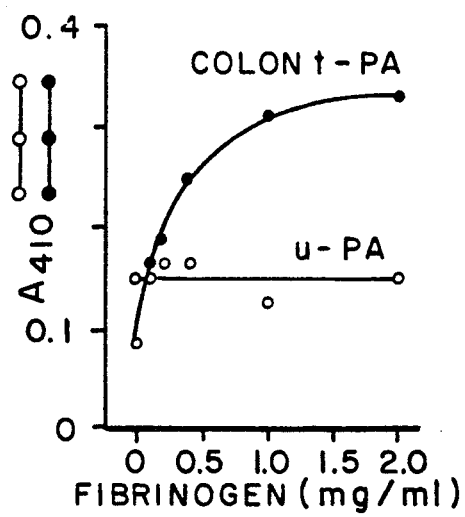
FIG. 1 shows the normal human colon cell t-PA assay results in which fibrinogen (mg/ml) is plotted against absorbance in a colorimetric assay for PA activity comparing the t-PA with commercially available u-PA.

In a preferred embodiment of the invention, plasminogen activator is isolated from the normal human colon fibroblast cell line CCD-18Co. Both urokinase plasminogen activator (u-PA) and tissue plasminogen activator (t-PA) are obtainable from the culture fluids of this cell line in large scale production lots. The colon u-PA has a molecular weight of about 54,000 whereas the colon t-PA has a molecular weight of about 67,000 daltons.

The CCD-18Co cell line is on deposit without restriction in the permanent collection of the American Type Culture Collection, Rockville, Maryland, under accession number ATCC CRL-1459. Samples of this cell line can be obtained by the public upon request to that depository.

This cell line was originally cultured in CRCM medium with 20% fetal bovine serum and antibiotics. CRCM is a nutrient medium developed by the American Type Culture Collection. During passage, the medium was changed to minimum essential medium (Eagle) with non-essential amino acids in Earle's BSS (balanced salt solution) supplemented with 10% fetal bovine serum. These cells also can be cultured in other well-known cell culture media such as basal medium Eagle's (BME), Dulbecco's modified Eagle medium (DMEM), medium 199, RPMI 1640 medium, and the like cell culture media such as described in detail by H.J. Morton, *In Vitro* 6, 89–108 (1970). These conventional culture media contain known amino acids, mineral salts, vitamins, hormones and carbohydrates. They are also frequently fortified with mammalian sera such as fetal bovine serum. Other components which are desirably used in the media are protein hydrolysates such as lactalbumin hydrolysate, tryptone, tryptose, peptone and the like materials.

Various other normal human colon fibroblast cell lines also can be used in accordance with the invention. Thus, another suitable normal human colon fibroblast cell line is the cell line designated CCD-112CoN which is available without restriction from the American Type Culture Collection under accession number ATCC CRL-1541.

Methods for the large scale growth of mammalian cells are well-known and these methods can be used for the culture of the colon cells defined herein. Such methods are described, for example, by Tolbert et al., *Biotech. Bioeng.* XXIV, 1671–1679 (1982); Tolbert and Feder, Ann. Rept. Ferm. Proc., Vol. 6, Ch. 3, pp. 35–74 (1983); Harakas, *Ibid.*, Vol. 7, Ch. 7, pp. 159–211 (1984); and references cited in said publications. U.S. Pat. Nos. 4,166,768; 4,289,854; 4,335,215; and 4,537,860 disclose particularly useful methods and apparatus for the large scale growth and maintenance of cells for the production of plasminogen activators. The disclosures in said patents are incorporated herein by reference. The methods and apparatus disclosed therein can be used for the culture of the colon cells defined herein.

The cells are preferably cultured in nutrient medium at 37° C. in agitated microcarrier suspension culture as described in U.S. Pat. No. 4,335,215 and, after a suitable growth period, are maintained in the static maintenance reactor described in U.S. Pat. No. 4,537,860 in which the medium is supplemented with 0.5% lactalbumin hydrolysate.

Purification of the plasminogen activator from the spent culture media can employ various known procedures for the separation of proteins such as, for example, salt and solvent fractionation, adsorption with colloidal materials, gel filtration, ion exchange chromatography, affinity chromatography, immunoaffinity chromatography, electrophoresis and high performance liquid chromatography (HPLC).

Procedures found to be particularly useful are affinity chromatography with zinc chelate-agarose, p-aminobenzamidine-agarose, concanavalin A-agarose (Con A-Sepharose ®), fibrin-diatomaceous earth (fibrin-Celite ®) and fibrin-agarose (fibrin-Sepharose); HPLC with a TSK 3000 SW size exclusion column; and immunoaffinity chromatography with monoclonal antibodies.

In a preferred process, the spent culture medium is subjected to zinc chelate-agarose affinity chromatography and affinity chromatography with either concanavalin A-agarose, or fibrin-Celite, or fibrin-agarose, followed by TSK 3000 SW size exclusion HPLC and p-aminobenzamidine agarose affinity chromatography of the PA activity.

In the affinity chromatography with zinc chelate-agarose, both u-PA and t-PA are bound to the column. Elution preferably is achieved with 50 mM imidazole. This step increases the plasminogen activator specific activity about 5 to 10 fold.

Separation of u-PA and t-PA is preferably accomplished in the next purification step using affinity chromatography with either concanavalin A-Sepharose, fibrin-Celite, or fibrin-Sepharose. The Con A-Sepharose column is preferably eluted with a linear gradient of the column equilibration buffer and equal volume of 0.4 M α-D-methylmannoside and 2 M KSCN. Alternatively, t-PA, but not u-PA, is bound to the fibrin-Celite or fibrin-Sepharose column and is preferably eluted with 0.2 M arginine.

The t-PA fraction from either the Con A-Sepharose, fibrin-Celite or fibrin-Sepharose affinity chromatography is further purified using TSK 3000 SW size exclusion HPLC followed by p-aminobenzamidine-agarose affinity chromatography.

The zinc chelate-agarose can be prepared essentially as described by Rijken and Collen, *J. Biol. Chem.* 256(13), 7035–7041 (1981) by coupling iminodiacetic acid to Sepharose ® 4B and saturating this material with zinc chloride (7.3 mM), regenerating with 0.05 M EDTA, pH 8.0, 0.05 M $NH_4HCO_3$, pH 10.5, and water, and resaturating with zinc chloride. Sepharose 6B, an agarose gel in bead form, 60–140μ wet bead diameter, available from Pharmacia Fine Chemicals, Inc., Piscataway, N.J., can be used in place of the Sepharose 4B. The chelating Sepharose 6B can be purchased from Pharmacia in pre-prepared form.

Con A-Sepharose is similarly available from Pharmacia Fine Chemicals, Inc., and is prepared by coupling concanavalin A to Sepharose 4B by the cyanogen bromide method. The Con A-Sepharose 4B also can be purchased from Pharmacia in pre-prepared form.

Para-aminobenzamidine-agarose is commercially available from Pierce Chemical Co., Rockford, Ill.

The TSK 3000 SW size exclusion HPLC employs a column of hydrophilic, spherical silica. It is commercially available from Toyo Soda Manufacturing Co., Ltd., Yamaguchi, Japan, and Beckman Laboratories, Fullerton, Calif. A preferred TSK 3000 SW column is Spherogel-TSK 3000 SWG which has a pore size of 250 Å±5%, a particle size of 13±2μ and a molecular weight fractionation range of 15,000 -150,000.

The fibrin-Celite is a fibrin affinity matrix prepared from Celite filter-aid which is a diatomaceous earth (diatomite) commercially available from Manville Filtration & Minerals, Denver, Colorado. This matrix can be prepared as described by Husain et al., *Proc. Natl. Acad. Sci. USA* 78, 4265-4269 (1981). According to this procedure, the Celite matrix surface is exposed to excess fibrinogen in a buffer and then to thrombin in a buffer to convert the fibrinogen to fibrin whereby the adsorptive surface is fully occupied by fibrin. Affinity chromatography on fibrin-Celite is used to remove non-fibrin binding proteins such as the urokinase plasminogen activator.

In the fibrin-Sepharose affinity chromatography, a matrix of fibrin is formed on Sepharose (agarose) instead of the Celite (diatomite).

In the immunoaffinity chromatography, monoclonal antibodies having an affinity for plasminogen activator are attached to polysaccharide beads which are then used as the chromatographic column. Monoclonal antibodies of Bowes t-PA immobilized on Sepharose 4B has been found useful in this chromatographic procedure.

Materials and methods used in the detailed examples set forth hereinafter are as follows:

Materials and Methods

General. Protein determinations were made by the method of Bradford, *Anal. Biochem.* 72, 248-254 (1976), using the BioRad protein determination kit, and BSA (bovine serum albumin - Sigma Fraction V) as standard. SDS-PAGE (sodium dodecyl sulfate polyacrylamide gel electrophoresis) was performed by the method of Laemmli, *Nature* 227, 680-685 (1970). The controls used were Bowes melanoma t-PA (American Diagnostica, Inc., Greenwich, CT; specific activity $$10^5 \frac{IU}{mg}$$

by WHO u-PA standard) and u-PA (Abbokinase ®, Abbott Laboratories, Chicago, Ill., $M_r=33,000$, clinical grade specific activity not given). For reduced samples, 25 mM dithiothreitol was included in the sample buffer. Protein was stained in the gels with either Coomassie brilliant blue R250, or with silver nitrate using the BioRad kit. Molecular weight standards (Pharmacia) were phosphorylase B ($M_r=94,000$), bovine serum albumin ($M_r=67,000$), ovalbumin ($M_r=43,000$), carbonic anhydrase ($M_r=30,000$), soybean trypsin inhibitor ($M_r=20,000$), and α-lactalbumin ($M_r=14,400$).

HPLC. A Hewlett-Packard 1090A liquid chromatograph or a Beckman system composed of a model 450 controller, two model 114M pumps for solvent delivery, and a model 165 variable wavelength detector were used for HPLC.

PA Spot Assays. Activity expressed as Ploug units per ml was determined by applying 5 μl of sample onto the surface of an agarose gel in petri dish containing fibrinogen, thrombin and plasminogen. The cloudy gel is cleared in an area proportional to the PA activity. PA activity was determined by reference to urokinase standards by a similar method by Haverkate and Brakman, *Progress in Chemical Fibrinolysis and Thrombosis*, Vol. I, ed. by Davidson et al., Raven Press, New York, 1975, pp. 151-159. To compare the thus determined PA activities for t-PA to the t-PA WHO standard, the values had to be multiplied by a factor of 30. This was determined by testing the t-PA WHO standard in the PA assay method used.

SDS-PAGE Electrophoresis Overlays. The molecular weight of the active moiety was estimated by non-reduced SDS-PAGE by the method of Laemmli, supra, then washing out the SDS and overlaying the polyacrylamide gel with a fibrinogen, thrombin, plasminogen, agarose gel (similar to that used in the spot assay). Molecular weight was calculated from included standards. The active regions clear the cloudy agarose gel. For background information, see Loskutoff and Mussoni, *Blood* 62(1), 62-68 (1983).

Assay of PA. For routine screening of column fractions for PA, either a fibrin-spot assay as described above or direct colorimetric assay in 96-well microtiter plates utilizing peptide substrates S-2322, D-Val-Gly-Arg-paranitroanilide (Kabi), or S-2288, D-Ile-Pro-Arg-paranitroanilide-dihydrochloride (Kabi), was carried out. For background information, see Wallen et al., *Eur. J Biochem.* 132, 681-686 (1983). A coupled assay using the plasmin peptide substrate S-2251, D-Val-Leu-Lys-paranitroanilide (Kabi), was used to measure fibrinogen stimulation of plasminogen activation by t-PA. See Verheijen et al., *Thromb. Heamostas.* 48, 266-269 (1982). In this assay, plasminogen (0.25 CU units, Kabi) and S-2251 (0.45 mM) were incubated with 60 units of colon t-PA or 50 units of commercially available u-PA (Abbott Abbokinase ®) in 200 μl of buffer containing 0.1 M potassium phosphate, pH 7.6, 0.1% BSA, and 0.01% Tween 80. After 10 minutes at room temperature, the absorbance at 410 nm was read. To measure fibrinogen stimulation, various amounts of fibrinogen were included in the assay.

Zinc Chelate-Sepharose Chromatography. The Zn-chelate-Sepharose chromatography was performed essentially as described by Rijken et al., supra. However, in some runs a batch procedure was used for binding the PA activity and column elution was used for recovery of the PA activity. The procedure was carried out in accordance with the following detailed instructions.

Resin Preparation

The zinc chelating Sepharose 6B was prepared as follows:

Wash a 20% ethanol solution of the resin with sterile H₂O. Use ten separate resin volumes to wash alcohol on a fritted Buchner funnel.

Resuspended Sepharose 6B resin as a 75% slurry in H₂O and allow to degas overnight at room temperature by tumbling in a rolling mill. Do not stir resin with a magnetic stirrer because beads may be damaged.

Use a sterile $ZnCl_2$ solution of 5 mg/ml at pH 5.0 to charge resin either on a column or on the fritted Buchner funnel. It takes about 1.5 to 2 resin volumes of the $ZnCl_2$ to saturate it. The resin is charged when the effluent shows a precipitate in a 10% $Na_2CO_3$ solution test indicating $Zn^{++}$. An alternate and preferred method for charging the resin is to lower resin pH to 5.0; add 1-2 volumes of $ZnCl_2$ (pH 5.0) to the resin and roll for 2-3 hours at 4° C. Check for precipitate of $Zn^{++}$ in supernatant as previously. Then, in either case, the excess $Zn^{++}$ is removed by washing with sterile Milli-Q $H_2O$, and the complete washing of the resin free of $Zn^{++}$ is indicated by the absence of a precipitate of the effluent $H_2O$ wash in 10% $Na_2CO_3$ solution. The thus charged resin is equilibrated with the column Buffer A (1.0 M NaCl+20 mM Tris-HCl+0.01% Tween 80 at pH 7.5), using pH as the indicator for equilibration. This can be done easily on a fritted Buchner funnel.

Plasminogen Activator (PA) Activity Binding

Batch Method

Use about 35 grams of equilibrated resin per liter of colon culture conditioned media (CM) at 4° C.

Add 0.01% (v/v) Tween 80 to CM if not already added. Use a 10% solution of Tween 80 which can be sterile filtered via a 0.2 μm Nalgene filter.

Add 100 units of penicillin per ml of CM and 100 μg of streptomycin per ml of CM.

Adjust CM pH to 7.5 using 0.1, or 1 N NaOH or 1 N HCl while CM is stirred gently using a stainless steel propeller 5.5 inches in diameter (Fisher Cat. No. 14-509-1).

Add appropriate amount of equilibrated resin to the CM and move CM vessel to 4° C. temperature room and allow to bind PA activity for 1.5 hours.

At end of 1.5 hours, turn stirrer off and allow resin to settle. The settling process takes about 1.5 hours for 100 liters of CM in a 100-liter working volume media vessel.

Pump unbound CM supernatant fraction to heat deactivation vessel.

Transfer resin and interstitial unbound CM to a 10-liter plastic container.

Add two resin volumes of Buffer A to resin and stir gently for 5 min.

At end of 5 minutes, turn off stirring and allow resin to settle. The resin settles in about 10-15 minutes and the supernatant is pumped to the deactivation tank.

About one resin volume of Buffer A is added to the resin in order to make a good slurry. This slurry is kept overnight at 4° C. in the closed sterile container.

Plasminogen Activator Elution: Column Method

The resin slurry is added slowly to a chromatographic column, e.g., with CM that requires 2 to 3 liters of resin, a 10 cm I.D. column with a resulting column height of 27 to 40 cm, respectively. The resin is allowed to settle well, and the unbound fraction is allowed to flow out at a flow rate of about 2-2.5 liters per hour.

The column is washed with at least two bed volumes of Buffer A at a rate of about 1.5 to 2 liters per hour (10 cm I.D. column) or until the $A_{280nm}$ absorbance is less than 0.2. An additional indication that the unbound fraction has been washed off the column is that the resin color changes from light red to very light brown.

The elution Buffer B is added. Buffer B is made up as follows:

20 mM Tris-HCl+1 M NaCl+0.01% (v/v) Tween 80 +50 mM Imidazole, pH 7.5.

The PA eluted activity is indicated by a zone of color brown and purple. The collection of the eluted fraction is started when the $A_{280nm}$ reading is >0.4.

The volume of the eluted fraction is about 0.7 to 0.95 of the column volume. The collection of the eluted fraction is terminated as indicated by the $A_{280nm}$ background reading and color of the bed which is pearly white when all the activity has been eluted. The rate at which the 10 cm I.D. column is eluted is about 2 liters per hour. Add 0.02% by wt. of $NaN_3$ to eluted fraction and freeze at $-35$ to $-40°$ C.

In still other runs of the Zn-chelate-Sepharose chromatography, the same general procedure was used as above, except that both binding and elution of PA activity was carried out continuously in a column operation using, for example, an 18 cm inside diameter column with 7 liters of Zn-chelate-Sepharose 6B resin.

Concanavalin A-Sepharose 4B Chromatography

Example 2 in Table 1 (see below):

Column used: I.D.=2.2 cm., Height=5 cm., Volume of Concanavalin A - Sepharose 4B=19 cc.

The column was equilibrated with Buffer C composed of 0.01 M potassium phosphate+1 M NaCl +0.01% (v/v) Tween 80 (Sigma, polyoxyethylenesorbitan monooleate), pH =7.5, at a rate of 38 ml/hour using more than seven column volumes.

The eluted fraction from the zinc chelate chromatography was applied to the column at 38 ml/hr (10 ml/hr/cm$^2$) and then the column was washed with Buffer C until there was negligible absorbance at 280 nm. indicating no protein present in the wash. Usually three to four column volumes were required to achieve such conditions.

Figure 9:
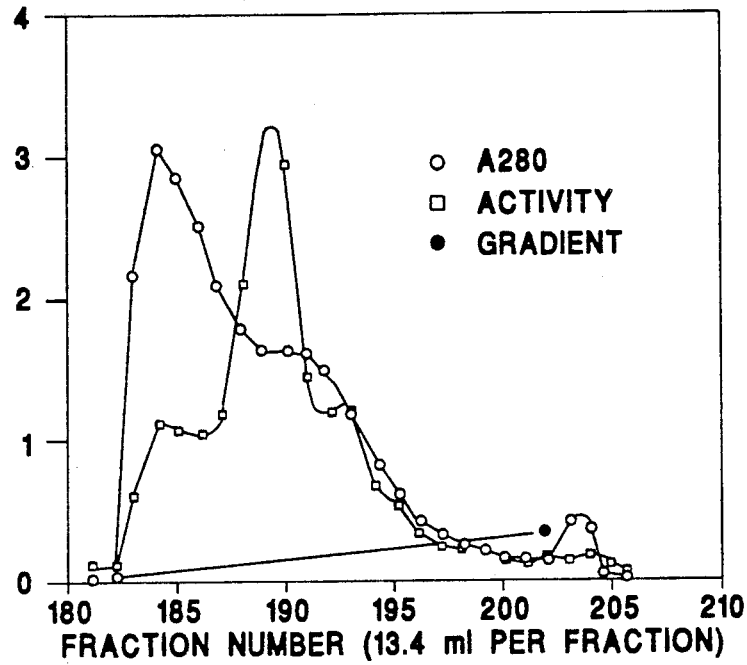
FIG. 9 shows chromatograms for Con A-Sepharose ® 4B fractionation for Example 2 and Table 1.

A linear gradient of 150 ml of Buffer C and 150 ml of a buffer composed of 2 M KSCN+0.4 M alpha-D-methyl mannoside+0.01 M potassium phosphate and 0.01% Tween 80, pH 7.5, was used to elute the t-PA activity. The elution rate was maintained at 38 ml/hr and 13.4 ml fractions were collected. Fractions 188 to 193 were pooled to yield 80 ml. The chromatograms for this fractionation are shown in FIG. 9.

Example 2 in Table 2 (see below):

Column used: I.D.=10 cm., Height=6.7 cm., Volume of Concanavalin A-Sepharose 4B =526 cc.

The column was equilibrated with Buffer C composed of 0.01 M potassium phosphate+1 M NaCl +0.01% (v/v) Tween 80 (Sigma, polyoxyethylenesorbitan monooleate), pH=7.5 at a rate of 13.1 ml/min. using more than seven column volumes.

The eluted fraction from the zinc chelate chromatography was applied to the column at 13.1 ml/hr (10 ml/hr/cm$^2$) and then the column was washed with Buffer C until there was negligible absorbance at 280 nm. indicating no protein present in the wash. Usually three to four column volumes were required to achieve such conditions.

Figure 10:
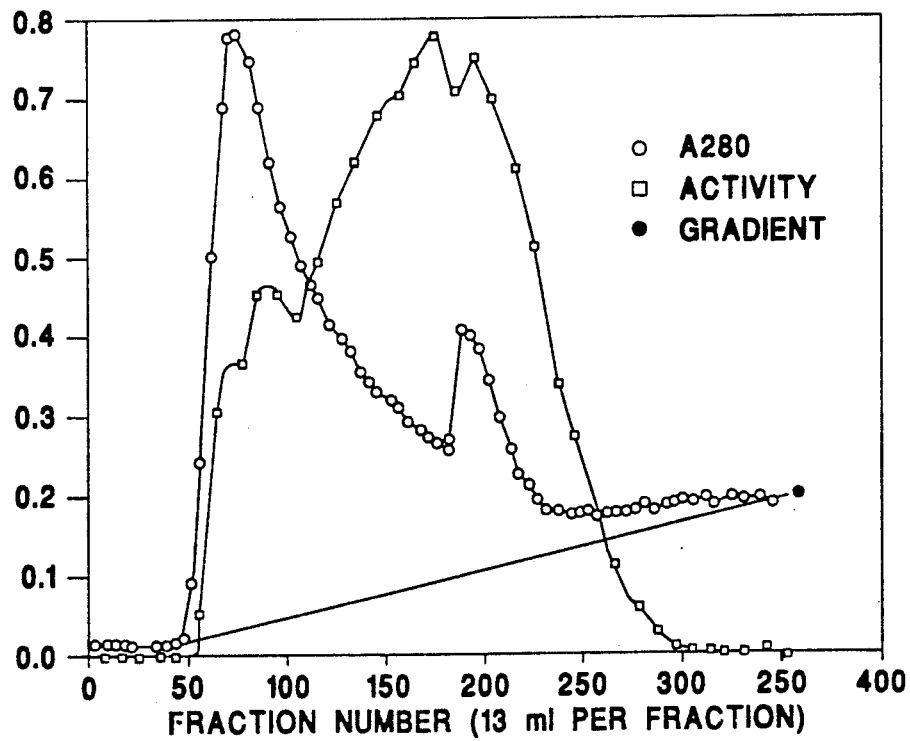
FIG. 10 shows chromatograms for Con A-Sepharose ® B fractionation for Example 2 and Table 2.

A linear gradient of 2.7 l of Buffer C and 2.7 l of a buffer composed of 2 M KSCN+0.4 M alpha-D-methyl mannoside+0.01 M potassium phosphate and 0.01% Tween 80, pH 7.5, was used to elute the t-PA activity. The elution rate was maintained at 13.1 ml/min and 13 ml fractions were collected. Fractions 118 to 230 were pooled to yield 1391 ml. The chromatograms for this fractionation are shown in FIG. 10.

Fibrin-Celite Affinity Chromatography. A fibrin affinity matrix was prepared using the procedure of Husain, supra. Twenty grams of Johns Manville Filter-Aid Celite (not acid washed) was washed in 4 liters of Milli-Q water. The water was poured off after allowing the material to settle for about two hours. This water wash was repeated three times. The liquid was removed from the Celite on a Buchner funnel and washed in the funnel with a liter of 50 mM potassium phosphate buffer, pH 7.5, containing 0.1 M sodium chloride and 1 mM ethylenediaminetetraacetic acid (EDTA). The Celite was suspended in 50 ml of buffer and stored at room temperature. 1.0 gram of Kabi fibrinogen "L grade" was processed over a lysine/ agarose column to remove plasminogen and stored frozen in 160 ml of 20 mM potassium phosphate buffer, pH 7.5, containing 0.3 M sodium chloride. The fibrinogen was brought to room temperature and sufficient EDTA added to make the solution 1 mM. Excess buffer was removed from the Celite on a Buchner funnel. The damp cake was added to the fibrinogen solution. The Celite suspended well without clumps. Slowly 250 units of thrombin was added with stirring (over 2-3 minutes). After 3 to 5 minutes the Celite began to take on the appearance of curdled milk. Stirring was continued, with difficulty, for a total of 15 minutes. Excess buffer was added and decanted until the excess fibrin was removed and the material could be washed on a Buchner funnel. The fibrin/Celite was washed with a liter of 10 mM potassium phosphate buffer, pH 7.5, containing 0.3 mM sodium chloride, 1 mM EDTA and 5 mM epsilon-aminocaproic acid. After pouring into a 1.5 centimeter diameter column, the fibrin/Celite was washed at a flow rate of 50 ml/hr with 500 ml of the above buffer, followed with 700 ml of the above buffer to which 0.2 M arginine was added and finally equilibrated with 500 ml of arginine-free buffer. The column had a total volume of about 60 ml and was stored ready for use at 4° C. The column was loaded with the colon Zn-Chelate fraction at a rate of 10 ml/hr, the column was washed with the above buffer and it was eluted with the above buffer with 0.2 M arginine at a rate of 10 ml/hr.

TSK 3000 SW Chromatography. Samples from the Con A-Sepharose step were dialyzed against 0.01% (w/v) Tween 80, lyophilized, and dissolved in 2–10 ml of buffer containing 20 mM sodium phosphate, pH 6.8, 1.6 M potassium thiocyanate, and 0.01% (w/v) Tween 80. Insoluble material was removed by centrifugation, and 2 ml samples were injected onto a Spherogel TSK 3000 SWG column (2.1 cm i.d.×60 cm l.). The flow rate was maintained at 5 ml per minute using the HPLC, and 4 ml fractions were collected into polystyrene tubes. Activity was measured using the colorimetric peptide substrate S-2322, D-Val-Gly-Arg-paranitroanilide (Kabi).

p-Aminobenzamidine Chromatography. Samples from the TSK 3000 SW step were dialyzed against 0.01% (w/v) Tween 80, lyophilized, and dissolved in 5 ml distilled H$_2$O. The samples were applied to a column (1.2 cm×10 cm) containing p-aminobenzamidine-agarose (Pierce) and washed with buffer containing 50 mM Tris-HCl, pH 8.0, 0.5 M NaCl, and 0.01% (w/v) Tween 80 at a flow rate of 0.5 ml per minute. After the A$_{280nm}$. reached baseline, the column was washed with two additional column volumes before eluting with the same buffer containing 1 M arginine. Fractions were assayed for t-PA activity using the substrate S-2322.

Purification of colon t-PA

The following examples will further illustrate the invention with greater detail in which t-PA was isolated in the large scale production of cultured normal human colon cells CCD-18Co.

EXAMPLE 1

CCD-18Co cells obtained from the American Type Culture Collection (ATCC CRL-1459) were grown at 37° C. in attached culture in 75 cmz T-flasks using Dulbecco's MEM high glucose medium supplemented with 10% fetal bovine serum. The resulting cells were then cultured at 37° C. in the same medium in large scale microcarrier suspension culture by the method of U.S. Pat. No. 4,335,215 using Corning Geli-Bead microcarriers. The cells, after a suitable growth period to provide $1.5 \times 10^{11}$ cells attached to microcarriers, were then maintained at 37° C. in serum-free conditioned media supplemented with 0.25–0.5% lactalbumin hydrolysate (LAH) in the static maintenance reactor (SMR) system of U.S. Pat. No. 4,537,860. About 1673 liters of crude serum-free conditioned media was recovered for product purification during a 4 month run of the SMR system.

EXAMPLE 2 t-PA was purified from the conditioned media of Example 1 as follows:

Table 1 below, shows the purification summary of t-PA from the normal human colon cells (CCD-18Co) in accordance with the above methods in one series of runs. In this series, the volume of Zn-chelate-Sepharose resin used to bind t-PA activity was 3500 ml. The volume of conditioned media was 96,000 ml using a 30 gallon stainless steel vessel with stirring. The processing steps for the Zn-chelate-Sepharose chromatography were as stated (see Materials and Methods Section) above with the following specific conditions:

Time of stirring=3 hours

Time for resin to settle=1.5 hours

Time to elute PA activity from resin in 10 cm inside diameter column=2 hours

Volume of eluate collected=2,000 ml.

The processing steps for the Con A-Sepharose chromatography were as stated (see Materials and Methods Section) above.

Table 2, below, shows the purification summary of t-PA from the normal human colon cells (CCD-18Co) in accordance with the above methods in another series of runs. In this series, the volume of Zn-chelate-Sepharose resin used to bind t-PA activity was 7 liters in an 18 cm diameter column. The rate of binding was 6.2 liters/hour. The elution rate was 5 liters/hour and the total volume of eluate was 13,000 ml. All other Zn-chelate-Sepharose column conditions and the processing steps for the Co A-Sepharose chromatography were as stated above (see Materials and Methods).

TABLE 1

Purification Summary of t-PA from CCD-18Co SMR Conditioned Media (CM) with DMEM + 0.5% LAH

| Process | Volume ml | PA PU/ml[b] | Coomassie Protein mg/ml | Total PA PU[b] | Total Protein mg | Sp. Act.[c] PU mg | Fold Purif. X |
|---|---|---|---|---|---|---|---|
| Starting CM loaded on Zn-Chelate | 96,000 | 10 | 0.033 | 960,000 | 3,168 | 303 | 1 |
| Zn-Chelate: Bound and Eluted (Zn-Fraction) | 2,300 | 290 | 0.172 | 667,000 | 396 | 1,684 | 5.6 |
| Zn-Fraction Loaded on Con A | 2,286 | 290 | 0.183 | 662,940 | 418 | 1,585 | 5.6 |
| Con A: Bound and Eluted t-PA (Con A-Fraction) | 80 | 1,589 | 0.721 | 3,813,600[a] | 57.7 | 66,120[a] | 218 |
| Con A-Fraction (½) Loaded, Dialyzed & Lyophilized (Tube A-Con A D/L) | 26.6 | 1,589 | 0.721 | 1,271,200[a] | 19.2 | 66,120[a] | 218 |
| Reconstituted Tube A-Con A D/L | 1 | 23,500 | 19.2 | 705,000[a] | 19.2 | 36,690[a] | 121 |
| Loaded on TSK 3000 SW Size Exclusion (HPLC) | 0.25 | 23,500 | 19.2 | 176,250[a] | 4.8 | 36,690[a] | 121 |
| t-PA TSK Fraction ($M_r = 67,000$) | 4 | 1,475 | 0.362 | 177,000[a] | 1.45 | 122,070[a] | 403 |

Footnotes below
[a]Fibrin plate assay value multiplied by 30 factor for comparison to the WHO t-PA standard. All corrected values are in IU/mg.
[b]PU = Ploug Units
[c]Sp. Act. = Specific Activity
D/L = Dialyzed and Lyophilized

TABLE 2

Purification Summary of t-PA from CCD-18Co Used for Canine Thrombolysis Test

| | Vol. (ml) | Protein (mg) | Activity Spot (UK PU) | Activity S-2288 (nmol/min.) |
|---|---|---|---|---|
| Cond. Medium | 260,000 | 8,540 | 700,000 | — |
| Zn-chelate eluate | 13,000 | 1,070 | 715,000 | — |
| Con-A peak | 1,391 | 100 | 125,000 | — |
| TSK Spent Media Applied to TSK column (TSK Starting Material) | 21.4 | 240 | — | 92,700 |
| TSK t-PA Peak | 140 | 50.4 | — | 52,800 |
| Benzamidine t-PA SM | 144 | 60.6 | — | 49,500 |
| Benzamidine peak | 40 | 18.6 | — | 35,400 |
| Dialyzed (+ filtered) | 59 | 15.8 | — | 27,700 |

The t-PA produced from normal human colon cells (CCD-18Co) and purified according to the foregoing methods was used in canine thrombolysis tests with two dogs. Prior to administration, the t-PA samples were dialyzed to prepare physiologically isotonic solutions. Thus, following elution from p-aminobenzamidine-agarose with 1 M arginine, the peak fractions (about 1.5 mg/ml protein) were diluted from 12 to 50 ml with 0.15 M NaCl, 0.01% Tween 80, and dialyzed (1:40) for 72 hours against 0.3 M NaCl, 1 mM sodium phosphate, 0.01% Tween 80, pH 6.8. Very little precipitation of protein was observed during this dialysis. The pH of the dialysate was 7.9. The dialyzed sample was then sterile filtered and stored at 4° C. for 8 days. The sample was then diluted with an equal volume of sterile 0.01% Tween 80, yielding a clear solution. After two days storage at 4° C., however, a precipitate was noted. Enough 3 M proline was then added by sterile filtration to yield a proline concentration of 20 mM. After several days at 4° C. a precipitate was still present. About 20 ml of 0.15 m NaCl, 0.01% Tween 80 were added and the solution was sterile filtered to give 129 ml of clear sample.

In accordance with these canine thrombolysis tests, an artificial thrombus was induced by advancing a 1×3 mm copper coil into the left anterior descending coronary artery distal to the first main diagonal branch. This procedure was carried out as described by Van de Werf et al., Circulation 69(3), 605-610 (1984). An occlusive thrombus formed at the site of the coil.

Presence and stability of the clot was confirmed by angiography. A 50 ml syringe pump was used to infuse t-PA solution via a midbody, intravenous catheter over a 60-minute period. Blood samples for assay of fibrinogen, t-PA antigen, and t-PA fibrinolytic activity were taken before t-PA infusion and at 5-minute intervals for 30 minutes following infusion. In one of the dog trials, the normal human colon t-PA was shown to be an effective thrombolytic agent in vivo without causing a systemic lytic state. In this trial, sample t-PA material from the series of runs shown in Table 2 was administered to the dog consecutively with additional samples of material from 2 other series of runs in which the affinity chromatography purification step with the p-aminobenzamidine-agarose was omitted.

In the other dog trial, clot lysis was not observed. The reason for this is unclear, but several factors are believed to have been important. First, the nature of the test requires that a different dog and a different thrombus be used for each trial. It is known that canine thrombi are sometimes resistant to treatment with t-PA for unknown reasons. Secondly, heparin was not administered with this trial whereas it was given 25 minutes after the beginning of the t-PA infusion in the successful dog trial. Heparin is typically used in such trials to prevent reocclusion as reported by Bergmann et al., Science 220, 1181-1183 (1983); and Van de Werf et al., Circulation 69(3), 605-610 (1984). Thirdly, the t-PA used in this trial was acid adjusted to pH 4 to improve its solubility and this may have caused the t-PA to be more susceptible to hepatic clearances. However, in both dog trials, there were no significant decreases in fibrinogen levels following t-PA infusion compared to preinfusion values, thus demonstrating the fibrin specificity of the t-PA.

EXAMPLE 3

Verification that the normal human colon cells (CCD-18Co) also produced u-PA, the authentic enzyme with $M_r=54,000$, was demonstrated by a polyclonal antibody of human urokinase and the Western blot immunological-electrophoresis technique (electroblotting) of Renart and Sandoval, *Methods in Enzymol.* 104, Academic Press, 1984, Part C, pp. 455-460. According to this procedure, 1 μg amounts of TSK 3000 SW purified t-PA, monoclonal antibody purified t-PA (as prepared in Example 4), American Diagnostica melanoma t-PA, Calbiochem u-PA, Abbott Laboratories u-PA and a molecular weight marker were subjected to SDS PAGE. The proteins were blotted onto activated paper and allowed to react with 1:3000 dilution of Green Cross anti-human urokinase rabbit serum (distributed by Alpha Therapeutic Corp., Los Angeles, Calif.). The immunolabeled proteins were labeled with radioiodine tagged Protein A. After washing, the radiolabeled immunolabeled paper was exposed to x-ray film. Any urokinase was evident as a dark spot on the x-ray film. Urokinase was evident in the TSK purified material and in the urokinase preparations but not in the monoclonal antibody purified t-PA or the American Diagnostica melanoma t-PA or in the molecular weight marker.

EXAMPLE 4

An alternate to the purification step of concanavalin A Sepharose-4B affinity chromatography to separate the two plasminogen activator molecules, u-PA and t-PA, is to use immunoaffinity chromatography and specifically using monoclonal antibodies (mcAb's) of Bowes t-PA immobilized on Sepharose-4B matrix. The process to purify colon t-PA with mcAb's was carried out as follows: 1 vial of American Diagnostica PAM-1/Sepharose (mcAb of Bowes t-PA, single chain) containing 10 mg IgG per 1.7 ml of gel was gently stirred for 4 hours at room temperature with 25 ml of colon Concanavalin A fraction dialyzed against water. The solution was filtered, washed and poured into a small column. After washing with PBS and 0.25 M KSCN, the t-PA was eluted with 1.6 M KSCN in PBS essentially following the recommendation of ADI (American Diagnostica Incorporated, Greenwich, CT) the manufacturer of the Bowes t-PA mcAb. Colon t-PA was also purified using the mcAb of two-chain t-PA of Bowes melanoma (PAM-2, manufactured by ADI). In the process for purification, the conditioned media of CCD-18Co samples were chromatographed on zinc-chelate Sepharose-6B and the bound plasminogen activators (u-PA and t-PA) fraction was chromatographed on p-aminobenzamidine Agarose, thus further purifying the u-PA/t-PA complex bound fraction. Said u-PA/t-PA fraction was fractionated into u-PA and t-PA via the PAM-2 mcAb in which u-PA was the unbound fraction and t-PA was the bound fraction which was eluted with 2 M KSCN.

EXAMPLE 5

An additional alternate to the purification step of concanavalin A-Sepharose 4B affinity chromatography to separate u-PA and t-PA is to use fibrin, to which the t-PA specifically binds, immobilized on Sepharose 4B. The process of the Fibrin/Sepharose Affinity Chromatography was carried out as follows: Fibrinogen was attached to cyanogen bromide treated Sepharose. Excess reactive sites were blocked with ethanolamine. The attached fibrinogen was converted to fibrin with thrombin. The beads were washed with and stored in PBS with 1 mM EDTA. A sample of colon t-PA zinc-chelate fraction was run over the Fibrin-Sepharose-4B column and the bound t-PA fraction was eluted with the buffer: 0.1 M NaCl+50 mM KHPO$_4$, pH 7.5,+1 mM EDTA+0.2 M arginine.

Characterization of Colon t-PA

FIG. 1 shows the colorimetric assay results in which fibrinogen (mg/ml) is plotted against absorbance. The activation of plasminogen by either colon t-PA or u-PA in the presence of varying amounts of fibrinogen using the plasmin substrate S-2251 confirms the unique activity of the t-PA compared with u-PA. The result is similar to that reported by Hoylaerts, et al., *J. Biol. Chem.* 257, 2912-2919 (1982) for t-PA derived from uterine tissue and Bowes melanoma cultured cells.

To illustrate the comparative peptide structure of t-PA of the present invention, reduced and carboxymethylated normal human colon t-PA (CCD-18Co) and Bowes melanoma t-PA were each subjected to HPLC on a reversed phase, VYDAC C-4 column. The column was obtained from The Separations Group, Hesperia, Calif. The HPLC elution profiles are shown in FIGS. 2 to 8, respectively, as follows.

Figure 2:
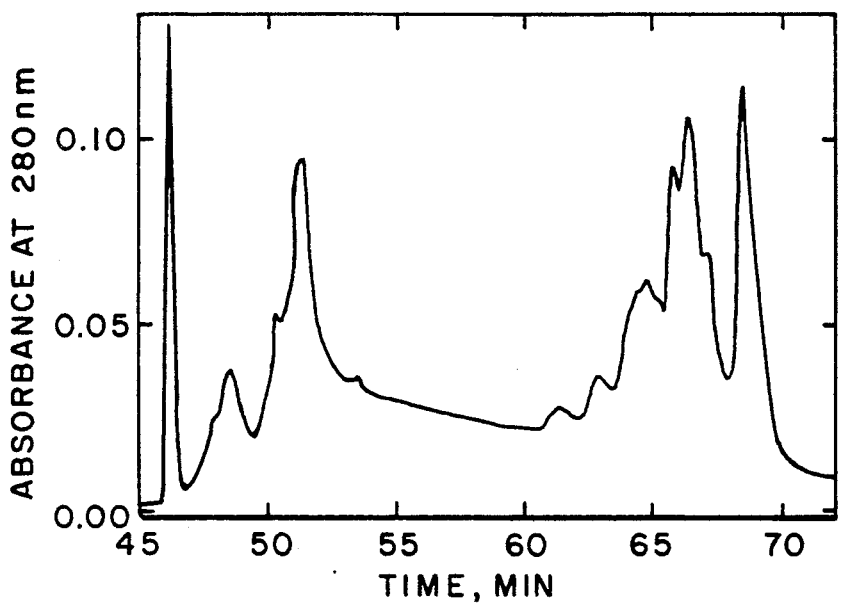
FIG. 2 shows the reversed phase HPLC of reduced and carboxymethylated normal human colon cell t-PA.

FIG. 2. Reversed-phase HPLC of reduced and carboxymethylated colon cell t-PA. Colon t-PA (1.1 mg in 1 M NH$_4$HCO$_3$) was lyophilized and carboxymethylated. The method of Pohl et al., *Biochem.* 23, 3701-3707 (1984) was used with modifications as follows. A buffer change to 1 M NH$_4$HCO$_3$ was accomplished by gel filtration on Sephadex G-25 (PD-10 column, Pharmacia) and the sample was lyophilized. It was then dissolved in 1 ml of 0.1% triflouroacetic acid (TFA). After standing overnight at 4° C, the sample (0.9 ml) was applied to the HPLC column. HPLC conditions: Vydac 214TP456 (C-4, 5μ, 300 Å, 4.6 ×250 mm) column; room temperature; 1 ml/min; gradient from 10% acetonitrile, 0.1% TFA at 0 min. to 60% acetonitrile, 0.1% TFA at 100 min. Fractions of 0.5 min (0.5 ml) were collected. The effluent was monitored at 280 nm.

Figure 3:
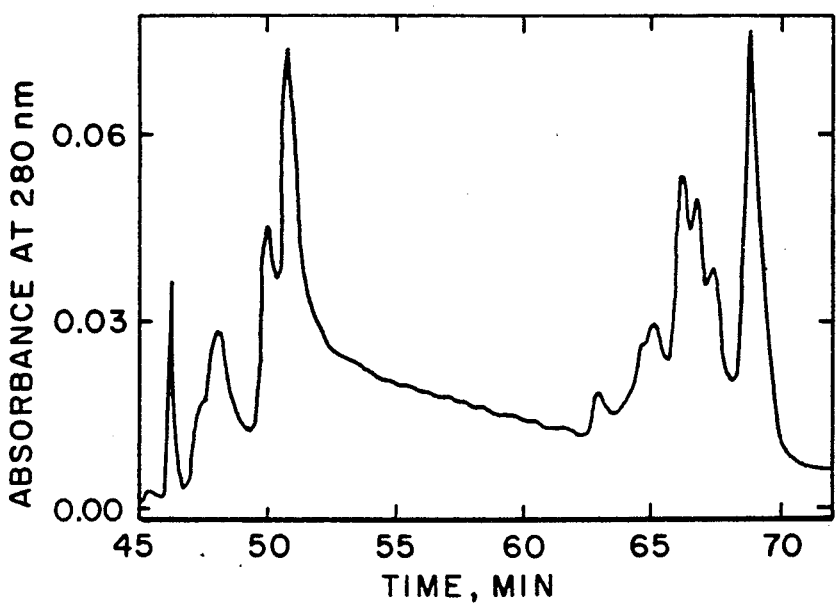
FIG. 3 shows the reversed phase HPLC of reduced and carboxymethylated Bowes melanoma t-PA.

FIG. 3. Reversed-phase HPLC of reduced and carboxymethylated Bowes malanoma t-PA. Bowes melanoma t-PA (American Diagnostia, Inc., product #110, approximately 1 mg in 1 M NH$_4$HCO$_3$) was lyophilized and treated in parallel with the colon t-PA sample exactly as described above with respect to FIG. 2. The carboxymethylated protein, however, did not completely dissolve in 0.1% TFA, so insoluble material was removed by centrifugation before injection on the HPLC column.

FIGS. 4.a. and 4.b. Reduced SDS-PAGE of HPLC fractions obtained during the separations described above for FIGS. 2 and 3. (a.) FIG. 4.a Fractions from chromatography of carboxymethylated Bowes melanoma t-PA, FIG. 3. (b.) FIG. 4.b Fractions from chromatography of carboxymethylated colon t-PA, FIG. 2. Pools were made of various fractions and 40 μl of each pool were applied to different lanes of the gel. Lane assignments are as follows for both FIGS. 4.a and 4.b and indicate the elution times between which fractions were pooled for each lane: (1) 46.0–47.0 min., (2) 47.0–49.5 min., (3) 49.5–52.5 min., (4) 52.5–57.5 min., (5) 57.5–62.5 min., (6) 62.5–65.5 min., (7) 65.5–68.0 min., (8) 68.0–70.0 min. Lane 9 is the sample applied to HPLC column and lane 10 contains molecular weight standards (94 K, 67 K, 43 K, 30 K, 20 K, and 14 K). The gel was stained with Coomassie blue.

Figure 5:
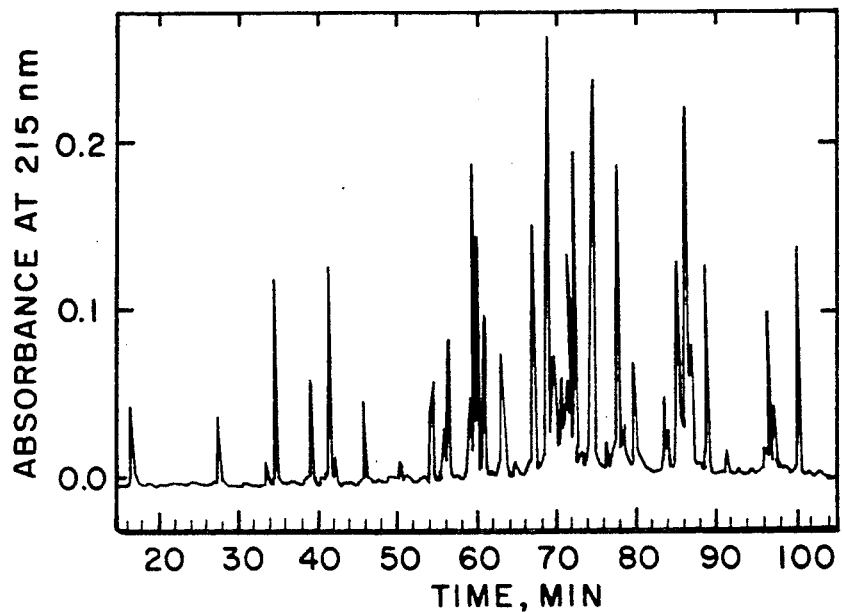
FIG. 5 shows the reversed phase HPLC of tryptic peptides from the carboxymethylated colon t-PA A chain.

FIG. 5. Reversed-phase HPLC of tryptic peptides from the carboxymethylated colon t-PA A chain. Fractions from 47.0 to 52.5 min. in FIG. 2 (total integrated absorbance at 280 nm: 203 mAU) were pooled and lyophilized. (mAU=milliabsorbance units.) The lyophilized material was dissolved in 0.1 M $NH_4HCO_3$ (0.5 ml) and 4.1 μg of trypsin (TPCK-treated, Sigma) were added. (TPCK=N-tosyl-L-phenylalanine chloromethyl ketone.) After 12 hr. at room temperature the sample was lyophilized. Immediately prior to injection on the HPLC column, the sample was dissolved in 0.5 ml 0.1% TFA. HPLC conditions: Nucleosil $C_{18}$, 5μ, 100Å, 4.6×250 mm column (Macherey-Nagel, Inc.); room temperature; 1 ml/min.; gradient elution from 0% acetonitrile, 0.1% TFA at 0 min. to 35% acetonitrile, 0.1% TFA at 105 min. Fractions of 2.0 ml (2.0 min) were collected. The effluent was monitored at 215 nm.

Figure 6:
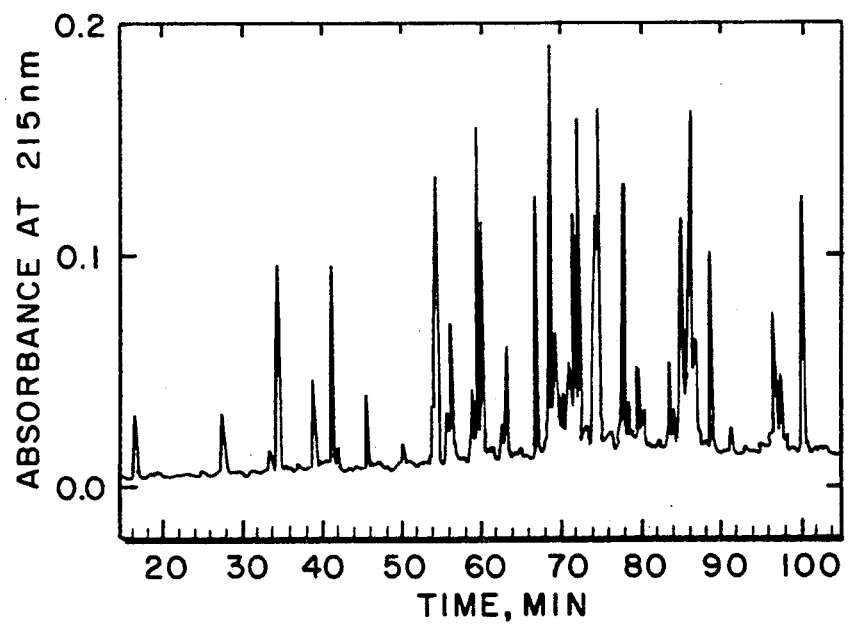
FIG. 6 shows the reversed phase HPLC of tryptic peptides from carboxymethylated Bowes melanoma t-PA A chain.

FIG. 6. Reversed-phase HPLC of tryptic peptides from carboxymethylated Bowes melanoma t-PA A chain. Fractions from 47.0 to 57.5 min. in FIG. 3. (total integrated absorbance at 280 nm: 151 mAU) were pooled and lyophilized. Trypsin treatment and HPLC were as described above with respect to FIG. 5, except that 3.0 μg trypsin were used for the digestion.

Figure 7:
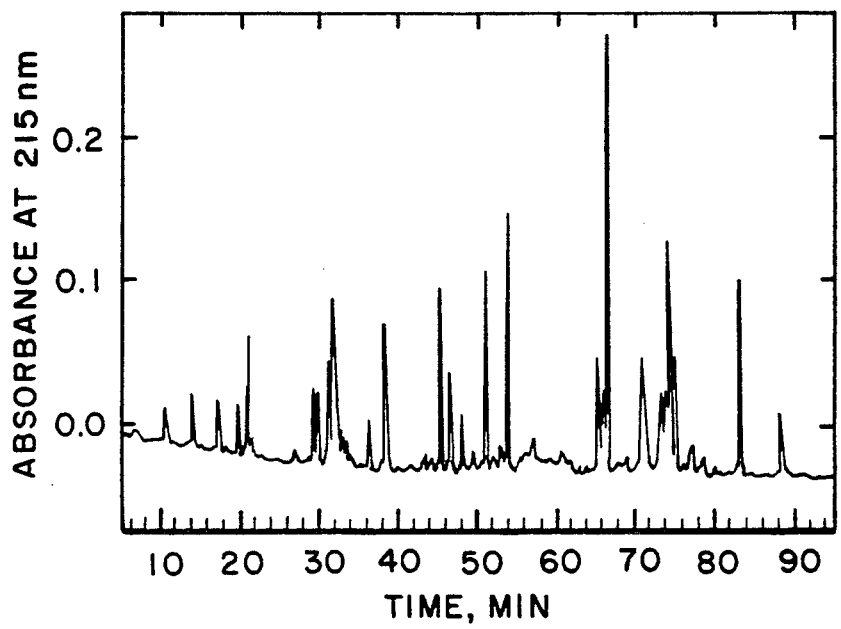
FIG. 7 shows the reversed phase HPLC of tryptic peptides from carboxymethylated colon t-PA B chain.

FIG. 7. Reversed-phase HPLC of tryptic peptides from carboxymethylated colon t-PA B chain. Fractions from 68.0 to 70.0 min. in FIG. 2 (total integrated absorbance at 280 nm: 107 mAU) were pooled and lyophilized. Treatment with trypsin and HPLC were as described above with respect to FIG. 5, except that 2.1 μg trypsin were used and the HPLC gradient was 0% acetonitrile, 0.1% TFA at 0 min. to 50% acetonitrile, 0.1% TFA at 100 min.

Figure 8:
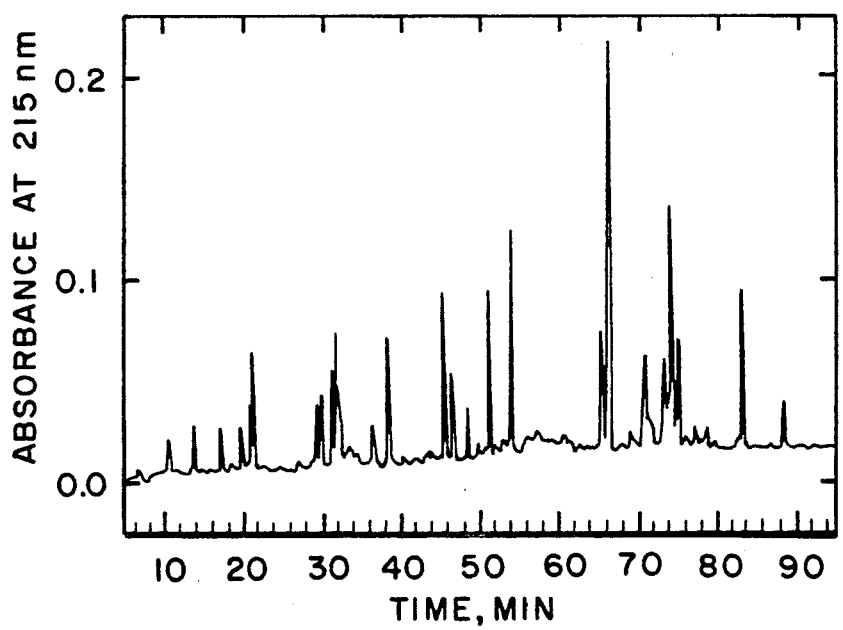
FIG. 8 shows the reversed phase HPLC of tryptic peptides from carboxymethylated Bowes melanoma t-PA B chain.

FIG. 8. Reversed-phase HPLC of tryptic peptides from carboxymethylated Bowes melanoma t-PA B chain. Fractions from 68.0 to 70.0 min. in FIG. 3 (total integrated absorbance at 280 nm: 66 mAU) were pooled and lyophilized. Treatment with trypsin and HPLC were as described above with respect to FIG. 5, except that 1.3 μg trypsin were used and the HPLC gradient was as described above with respect to FIG. 7.

When colon t-PA or melanoma t-PA were reduced and carboxymethylated and subjected to reversed-phase HPLC the resulting elution profiles shown in FIGS. 2 and 3, respectively, were very similar to each other. When pools of fractions corresponding to different sections of these elution profiles were analyzed by SDS-PAGE (sodium dodecyl sulfate, polyacrylamide gel electrophoresis) it was found that the peaks eluting between 47–53 min. contained a mixture of type I and II A chains and that the peak eluting between 68–70 min. contained B chain (FIG. 4.a. and 4.b.). Greater amounts of single chain t-PA were evident in the colon material than in the melanoma preparation, and the colon species eluted in the peaks between 63 and 68 minutes (FIGS. 4.a. 4b). The fractions corresponding to A and B chains of the colon t-PA (FIG. 2) or Bowes melanoma t-PA (FIG. 3) were digested with trypsin and the resulting peptides separated by HPLC (FIGS. 5–8). The A and B chain profiles for colon and Bowes melanoma t-PA were very similar and no major differences in the B chain profiles were apparent (FIGS. 7 and 8). The A chain profiles, however, differed in that (1) an additional peptide (eluting at 60.9 minutes) was present in the colon A chain profile and (2) a larger amount of the peptide eluting at 54.4 min. appears to be present in the Bowes melanoma A chain profile. The general conclusion from these analyses, however, is that colon t-PA and melanoma t-PA are substantially similar in terms of their amino acid sequence.

Background information on the general techniques and use of HPLC for the isolation and structural study of biologically active peptides as employed herein can be had by reference to common texts such as Hearn et al., *High-Performance Liquid Chromatography of Proteins and Peptides*, Academic Press, Inc., 1983. For background information on reverse phase HPLC separation of Bowes melanoma PA tryptic peptides and protein sequence determination, see Pohl et al., *Biochemistry* 23, 3701–3707 (1984).

Various other examples will be apparent to the person skilled in the art after reading the present disclosure without departing from the spirit and scope of the invention and it is intended that all such further examples are included within the scope of the appended claims.

What is claimed is:

1. A process for producing human tissue plasminogen activator which comprises culturing in vitro normal human colon fibroblast CCD-18Co (ATCC-1459) cells in nutrient culture medium, subjecting the resulting conditioned medium to a first affinity chromatography with zinc chelate-agrose and then a second affinity chromatography with material selected from the group consisting of (a) concanavalin A-agarose, (b) fibrin-Celite, and (c) fibrin-agarose, followed by TSK 3000 SW size exclusion high performance liquid chromatography and p-aminobenzamidine-agarose affinity chromatography and recovering the resulting purified tissue plasminogen activator in biologically active form separated from the urokinase.

2. The process of claim 1 in which the second affinity chromatography is carried out with concanavalin A-agarose.

3. The process of claim 1 in which the second affinity chromatography is carried out with fibrin-agarose.

4. The process of claim 1 in which tissue plasminogen activator is recovered by elution from a p-aminobenzamidine-agarose affinity chromatographic column with arginine.

5. The process of claim 2 in which tissue plasminogen activator is recovered by elution from a p-aminobenzamidine-agarose affinity chromatographic column with arginine.

6. A process for producing human tissue plasminogen activator which comprises culturing in vitro normal human colon fibroblast CCD-18Co (ATCC-1459) cells in nutrient culture medium, subjecting the resulting conditioned medium to a first affinity chromatography with zinc chelate-agrose and then a second affinity chromatography with concanavalin A-agarose, followed by TSK 3000 SW size exclusion high performance liquid chromatography and recovering the resulting tissue plasminogen activator in a purity exhibited by a single band at 67,000 daltons when subjected to SDS-PAGE analysis.

* * * * *